US008606357B2

(12) United States Patent
Lee et al.

(10) Patent No.: US 8,606,357 B2
(45) Date of Patent: Dec. 10, 2013

(54) CARDIAC WAVEFORM TEMPLATE CREATION, MAINTENANCE AND USE

(75) Inventors: Kent Lee, Singapore (SG); Robert Sweeney, Woodbury, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 872 days.

(21) Appl. No.: 12/341,558

(22) Filed: Dec. 22, 2008

(65) Prior Publication Data

US 2009/0105778 A1    Apr. 23, 2009

Related U.S. Application Data

(63) Continuation of application No. 10/448,260, filed on May 28, 2003, now Pat. No. 7,477,932.

(51) Int. Cl.
*A61N 1/37* (2006.01)

(52) U.S. Cl.
USPC .......................................................... 607/28

(58) Field of Classification Search
USPC ..................................................... 607/27, 28
See application file for complete search history.

(56) References Cited

U.S. PATENT DOCUMENTS

| | | |
|---|---|---|
| 3,920,005 A | 11/1975 | Gombrich et al. |
| 4,023,564 A | 5/1977 | Valiquette et al. |
| 4,365,636 A | 12/1982 | Barker |
| 4,458,692 A | 7/1984 | Simson |
| 4,552,154 A | 11/1985 | Hartlaub |
| 4,562,841 A | 1/1986 | Brockway et al. |
| 4,648,407 A | 3/1987 | Sackner |
| 4,680,708 A | 7/1987 | Ambos et al. |
| 4,827,935 A | 5/1989 | Geddes et al. |
| 4,860,766 A | 8/1989 | Sackner |
| 4,878,497 A | 11/1989 | Callaghan et al. |
| 4,928,688 A | 5/1990 | Mower |
| 5,000,189 A | 3/1991 | Throne et al. |
| 5,036,849 A | 8/1991 | Hauck et al. |

(Continued)

FOREIGN PATENT DOCUMENTS

| | | |
|---|---|---|
| EP | 0468720 | 1/1992 |
| EP | 0940155 | 9/1999 |

(Continued)

OTHER PUBLICATIONS

Office Action from U.S. Appl. No. 10/448,260 dated Jan. 11, 2006, 23 pages.

(Continued)

*Primary Examiner* — George Evanisko
(74) *Attorney, Agent, or Firm* — Brooks, Cameron & Huebsch, PLLC

(57) ABSTRACT

The present disclosure describes methods and systems for creating, adjusting, and using cardiac waveform morphology templates. The morphology templates include target regions associated with features of cardiac waveforms. The target regions may be adjusted based on relationships between the target regions and features of detected cardiac waveforms associated with the target regions. The templates may be used to analyze cardiac waveforms to classify or monitor various waveform morphologies. Templates may be created or eliminated based on a frequency of use. According to one approach, template creation involves providing target regions defined by one or more characteristics. The target regions are adjusted based on detected cardiac waveform features having similar characteristics. A template may be created using the target regions adjusted by this process.

20 Claims, 13 Drawing Sheets

(56) References Cited

U.S. PATENT DOCUMENTS

| | | |
|---|---|---|
| 5,101,831 A | 4/1992 | Koyama et al. |
| 5,105,354 A | 4/1992 | Nishimura |
| 5,146,918 A | 9/1992 | Kallok et al. |
| 5,178,156 A | 1/1993 | Takishima et al. |
| 5,184,615 A | 2/1993 | Nappholz et al. |
| 5,187,657 A | 2/1993 | Forbes |
| 5,203,348 A | 4/1993 | Dahl et al. |
| 5,217,021 A | 6/1993 | Steinhaus et al. |
| 5,222,493 A | 6/1993 | Sholder |
| 5,230,337 A | 7/1993 | Dahl et al. |
| 5,233,983 A | 8/1993 | Markowitz |
| 5,271,411 A | 12/1993 | Ripley et al. |
| 5,284,136 A | 2/1994 | Hauck et al. |
| 5,301,677 A | 4/1994 | Hsung |
| 5,313,953 A | 5/1994 | Yomtov et al. |
| 5,324,310 A | 6/1994 | Greeninger et al. |
| 5,334,222 A | 8/1994 | Salo et al. |
| 5,335,657 A | 8/1994 | Terry, Jr. et al. |
| 5,350,410 A | 9/1994 | Kleks et al. |
| 5,353,788 A | 10/1994 | Miles |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,411,031 A | 5/1995 | Yomtov |
| 5,411,529 A | 5/1995 | Hudrlik |
| 5,431,693 A | 7/1995 | Schroeppel |
| 5,443,485 A | 8/1995 | Housworth et al. |
| 5,447,519 A | 9/1995 | Peterson |
| 5,485,851 A | 1/1996 | Erickson |
| 5,517,983 A | 5/1996 | Deighan et al. |
| 5,522,860 A | 6/1996 | Molin et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson |
| 5,603,732 A | 2/1997 | Dahl et al. |
| 5,626,620 A | 5/1997 | Kieval et al. |
| 5,683,431 A | 11/1997 | Wang |
| 5,683,434 A | 11/1997 | Archer |
| 5,715,812 A | 2/1998 | Deighan et al. |
| 5,738,102 A | 4/1998 | Lemelson |
| 5,779,645 A | 7/1998 | Olson et al. |
| 5,814,087 A | 9/1998 | Renirie |
| 5,817,027 A | 10/1998 | Arand et al. |
| 5,836,987 A | 11/1998 | Baumann et al. |
| 5,855,593 A | 1/1999 | Olson et al. |
| 5,857,977 A | 1/1999 | Caswell et al. |
| 5,860,918 A | 1/1999 | Schradi et al. |
| 5,861,011 A | 1/1999 | Stoop |
| 5,876,353 A | 3/1999 | Riff |
| 5,916,243 A | 6/1999 | KenKnight et al. |
| 5,944,680 A | 8/1999 | Christopherson et al. |
| 5,964,778 A | 10/1999 | Fugoso et al. |
| 5,974,340 A | 10/1999 | Kadhiresan |
| 6,016,442 A | 1/2000 | Hsu et al. |
| 6,026,320 A | 2/2000 | Carlson et al. |
| 6,038,474 A | 3/2000 | Zhu et al. |
| 6,044,298 A | 3/2000 | Salo et al. |
| 6,045,513 A | 4/2000 | Stone et al. |
| 6,052,620 A | 4/2000 | Gillberg et al. |
| 6,055,454 A | 4/2000 | Heemels |
| 6,064,910 A | 5/2000 | Andersson et al. |
| 6,076,014 A | 6/2000 | Alt |
| 6,076,015 A | 6/2000 | Hartley et al. |
| 6,091,973 A | 7/2000 | Colla et al. |
| 6,101,416 A | 8/2000 | Sloman |
| 6,120,441 A | 9/2000 | Griebel |
| 6,126,611 A | 10/2000 | Bourgeois et al. |
| 6,128,534 A | 10/2000 | Park et al. |
| 6,128,535 A | 10/2000 | Maarse |
| 6,132,384 A | 10/2000 | Christopherson et al. |
| 6,141,581 A | 10/2000 | Olson et al. |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,190,326 B1 | 2/2001 | McKinnon et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,238,419 B1 | 5/2001 | Lindgren |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,270,457 B1 | 8/2001 | Bardy |
| 6,272,377 B1 | 8/2001 | Sweeney et al. |
| 6,275,731 B1 | 8/2001 | Zhu et al. |
| 6,277,072 B1 | 8/2001 | Bardy |
| 6,280,380 B1 | 8/2001 | Bardy |
| 6,285,907 B1 | 9/2001 | Kramer et al. |
| 6,299,581 B1 | 10/2001 | Rapoport et al. |
| 6,312,378 B1 | 11/2001 | Bardy |
| 6,312,388 B1 | 11/2001 | Marcovecchio et al. |
| 6,324,427 B1 | 11/2001 | Florio |
| 6,336,903 B1 | 1/2002 | Bardy |
| 6,345,201 B1 | 2/2002 | Sloman et al. |
| 6,351,669 B1 | 2/2002 | Hartley et al. |
| 6,353,759 B1 | 3/2002 | Hartley et al. |
| 6,358,203 B2 | 3/2002 | Bardy |
| 6,363,270 B1 | 3/2002 | Colla et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,393,316 B1 | 5/2002 | Gillberg et al. |
| 6,398,728 B1 | 6/2002 | Bardy |
| 6,411,848 B2 | 6/2002 | Kramer et al. |
| 6,415,183 B1 | 7/2002 | Scheiner et al. |
| 6,418,343 B1 | 7/2002 | Zhang et al. |
| 6,424,865 B1 | 7/2002 | Ding |
| 6,434,417 B1 | 8/2002 | Lovett |
| 6,434,428 B1 | 8/2002 | Sloman et al. |
| 6,438,410 B2 | 8/2002 | Hsu et al. |
| 6,440,066 B1 | 8/2002 | Bardy |
| 6,449,503 B1 | 9/2002 | Hsu |
| 6,456,881 B1 | 9/2002 | Bornzin et al. |
| 6,459,929 B1 | 10/2002 | Hopper et al. |
| 6,466,820 B1 | 10/2002 | Juran et al. |
| 6,480,733 B1 | 11/2002 | Turcott |
| 6,480,734 B1 | 11/2002 | Zhang et al. |
| 6,487,443 B2 | 11/2002 | Olson et al. |
| 6,493,586 B1 | 12/2002 | Stahmann et al. |
| 6,505,071 B1 | 1/2003 | Zhu et al. |
| 6,512,953 B2 | 1/2003 | Florio et al. |
| 6,542,775 B2 | 4/2003 | Ding et al. |
| 6,567,701 B2 | 5/2003 | Vonk |
| 6,574,507 B1 | 6/2003 | Bonnet |
| 6,589,188 B1 | 7/2003 | Street et al. |
| 6,595,927 B2 | 7/2003 | Pitts-Crick et al. |
| 6,597,951 B2 | 7/2003 | Kadhiresan et al. |
| 6,600,949 B1 | 7/2003 | Turcott |
| 6,615,082 B1 | 9/2003 | Mandell |
| 6,618,619 B1 | 9/2003 | Florio et al. |
| 6,641,542 B2 | 11/2003 | Cho et al. |
| 6,654,637 B2 | 11/2003 | Rouw et al. |
| 6,658,293 B2 | 12/2003 | Vonk |
| 6,684,100 B1 | 1/2004 | Sweeney et al. |
| 6,731,973 B2 | 5/2004 | Voith |
| 6,731,983 B2 | 5/2004 | Ericksen et al. |
| 6,731,984 B2 | 5/2004 | Cho et al. |
| 6,738,669 B1 | 5/2004 | Sloman et al. |
| 6,768,924 B2 | 7/2004 | Ding et al. |
| 6,773,404 B2 | 8/2004 | Poezevera et al. |
| 6,830,548 B2 | 12/2004 | Bonnet et al. |
| 6,881,192 B1 | 4/2005 | Park |
| 6,885,893 B1 | 4/2005 | Lu |
| 6,890,306 B2 | 5/2005 | Poezevera |
| 6,895,274 B2 | 5/2005 | Mower |
| 6,904,320 B2 | 6/2005 | Park et al. |
| 6,928,324 B2 | 8/2005 | Park et al. |
| 6,944,495 B2 | 9/2005 | MacAdam et al. |

(56) References Cited

U.S. PATENT DOCUMENTS

| | | |
|---|---|---|
| 6,950,702 B2 | 9/2005 | Sweeney |
| 6,959,214 B2 | 10/2005 | Pape et al. |
| 6,973,350 B1 | 12/2005 | Levine et al. |
| 6,975,904 B1 | 12/2005 | Sloman |
| 6,999,817 B2 | 2/2006 | Park et al. |
| 7,006,869 B2 * | 2/2006 | Bradley ................. 607/28 |
| 7,025,730 B2 | 4/2006 | Cho et al. |
| 7,027,868 B2 | 4/2006 | Rueter et al. |
| 7,027,871 B2 | 4/2006 | Burnes et al. |
| 7,081,095 B2 | 7/2006 | Lynn et al. |
| 7,094,207 B1 | 8/2006 | Koh |
| 7,103,404 B2 | 9/2006 | Staler et al. |
| 7,113,823 B2 | 9/2006 | Yonce et al. |
| 7,115,097 B2 | 10/2006 | Johnson |
| 7,117,036 B2 | 10/2006 | Florio |
| 7,127,290 B2 | 10/2006 | Girouard et al. |
| 7,155,278 B2 | 12/2006 | King et al. |
| 7,160,252 B2 | 1/2007 | Cho et al. |
| 7,177,689 B2 | 2/2007 | Ternes et al. |
| 7,179,229 B1 | 2/2007 | Koh |
| 7,191,003 B2 | 3/2007 | Greenhut et al. |
| 7,191,004 B2 | 3/2007 | Kim et al. |
| 7,203,543 B2 | 4/2007 | Meyer et al. |
| 7,212,862 B2 | 5/2007 | Park et al. |
| 7,225,021 B1 | 5/2007 | Park et al. |
| 7,248,921 B2 | 7/2007 | Palreddy et al. |
| 7,286,876 B2 | 10/2007 | Yonce et al. |
| 7,308,311 B2 | 12/2007 | Sorensen et al. |
| 7,319,900 B2 | 1/2008 | Kim et al. |
| 7,330,761 B2 | 2/2008 | Zhang |
| 7,337,000 B2 | 2/2008 | Meyer et al. |
| 7,369,889 B2 | 5/2008 | Astrom et al. |
| 7,438,686 B2 | 10/2008 | Cho et al. |
| 7,468,040 B2 | 12/2008 | Hartley et al. |
| 7,477,932 B2 | 1/2009 | Lee et al. |
| 2002/0002327 A1 | 1/2002 | Grant et al. |
| 2003/0195571 A1 | 10/2003 | Burnes et al. |
| 2003/0199945 A1 | 10/2003 | Ciulla |
| 2003/0204146 A1 | 10/2003 | Carlson |
| 2003/0204213 A1 | 10/2003 | Jensen et al. |
| 2004/0172065 A1 | 9/2004 | Sih et al. |
| 2004/0215277 A1 | 10/2004 | Oosterhoff et al. |
| 2004/0260351 A1 | 12/2004 | Holmstrom et al. |
| 2005/0004612 A1 | 1/2005 | Scholten et al. |
| 2005/0043652 A1 | 2/2005 | Lovett et al. |
| 2005/0085865 A1 | 4/2005 | Tehrani |
| 2005/0113710 A1 | 5/2005 | Stahmann et al. |
| 2005/0131477 A1 | 6/2005 | Meyer et al. |
| 2005/0131478 A1 | 6/2005 | Kim et al. |
| 2006/0129194 A1 | 6/2006 | Zhang |
| 2006/0129196 A1 | 6/2006 | Dong et al. |
| 2006/0241706 A1 | 10/2006 | Yonce et al. |
| 2007/0142741 A1 | 6/2007 | Berthon-Jones et al. |
| 2007/0239057 A1 | 10/2007 | Pu et al. |
| 2009/0163973 A1 | 6/2009 | Meyer et al. |

FOREIGN PATENT DOCUMENTS

| | | |
|---|---|---|
| EP | 1151718 | 11/2001 |
| EP | 1291038 | 3/2003 |
| EP | 1430930 | 6/2004 |
| JP | 6502778 | 3/1994 |
| WO | WO0001438 | 1/2000 |
| WO | WO0017615 | 3/2000 |
| WO | WO02087696 | 11/2002 |
| WO | WO2004026398 | 4/2004 |
| WO | WO2005058412 | 6/2005 |
| WO | WO2006065707 | 6/2006 |

OTHER PUBLICATIONS

Office Action from U.S. Appl. No. 10/448,260 dated Nov. 16, 2006, 8 pages.

Office Action from U.S. Appl. No. 10/448,260 dated Aug. 8, 2007, 8 pages.

Office Action from U.S. Appl. No. 10/448,260 dated Feb. 5, 2008, 9 pages.

File History for U.S. Appl. No. 12/396,267 as retrieved from U.S. Patent and Trademark Office on Mar. 1, 2011, 110 pages.

Ajilore et al., *Nightcap: Laboratory and home-based evaluation of a portable sleep monitor*, 32 Psychophysiology, 32-98, 1995. Abstract only.

Cohen et al. Capture Management Efficacy in children and young adults with endocardial and unipolar epicardial systems. Europace, vol. 6, pp. 248-255, 2004.

Splett et al., Determination of Pacing Capture in Implantable Defibrillators: Benefit of Evoked Response Detection Using RV Coil to Can Vector, PACE, vol. 23, pp. 1645-1650, 2002.

Verrier et al., Sleep, dreams, and sudden death: the case for sleep as an autonomic stress test for the heart, 31 Cardiovascular Research 181-211, 1996.

Verrier et al., Sleep Related Cardiovascular Risk: New Home-Based Monitoring Technology for Improved Diagnosis and Therapy, 2 A.N. E.158-175, 1997.

Waldemark et al., Detection of Apnea using Short Window FFT Technique and Artificial Neural Network, 3390 SPIE International Society for Optical Engineering 122-133, 1998. (partial article).

Notice of Allowance dated Sep. 8, 2008 from U.S. Appl. No. 10/448,260, 8 pages.

Office Action Response dated Jun. 9, 2008 from U.S. Appl. No. 10/448,260, 18 pages.

Nov. 13, 2007 Office Action Response dated Nov. 13, 2007 from U.S. Appl. No. 10/448,260, 15 pages.

Office Action Response dated Sep. 16, 2006 from U.S. Appl. No. 10/448,260, 15 pages.

Office Action dated Aug. 15, 2006 from U.S. Appl. No. 10/448,260, 8 pages.

Office Action Response dated Apr. 17, 2006 from U.S. Appl. No. 10/448,260, 20 pages.

May 29, 2012, File history for U.S. Appl. No. 12/008,876, 261 pages.

May 29, 2012, File history for U.S. Appl. No. 12/396,267, 187 pages.

Office Action dated Jul. 12, 2011 for Japanese patent application No. 2007-546821, 4 pages. (with translation).

Jul. 25, 2012, File History for U.S. Appl. No. 12/396,267, 217 pages.

Sep. 22, 2012, File History for U.S. Appl. No. 12/396,267, 229 pages.

\* cited by examiner

CARDIAC WAVEFORM TEMPLATE CREATION, MAINTENANCE AND USE

RELATED PATENT DOCUMENTS

This application is a continuation of U.S. patent application Ser. No. 10/448,260 filed on May 28, 2003, now U.S. Pat. No. 7,477,932, to which Applicant claims priority under 35 U.S.C. §120, and which is incorporated herein by reference in its entirety.

FIELD OF THE INVENTION

The present invention relates generally to methods and systems for creating, maintaining, and using cardiac morphology templates.

BACKGROUND OF THE INVENTION

Proper cardiac function relies on the synchronized contractions of the heart at regular intervals. When the heart is functioning normally, synchronized cardiac contractions are initiated at the sinoatrial node and the heart is said to be operating in normal sinus rhythm. However, if contractions of the heart become irregular or uncoordinated, or if the contraction rate is too fast or too slow, the heart rhythm is described as arrhythmic. Cardiac arrhythmia may be caused, for example, by disease processes or from aberrant electrical conduction patterns occurring in the heart tissue. Cardiac arrhythmia impairs cardiac pumping efficiency and some types of cardiac arrhythmia can be life threatening.

A cardiac arrhythmia that originates in an atrial region of the heart is denoted a supra-ventricular tachyarrhythmia (SVT). Atrial fibrillation and atrial flutter are examples of SVT. Both conditions are characterized by rapid, uncoordinated contractions of the atria resulting in hemodynamically inefficient pumping action.

Cardiac arrhythmias originating in a ventricular region of the heart are denoted ventricular tachyarrhythmias. Ventricular tachycardia (VT) is characterized by rapid ventricular contractions and can degenerate into ventricular fibrillation (VF). Ventricular fibrillation produces extremely rapid, non-coordinated contractions of the ventricles. Ventricular fibrillation is fatal unless the heart is returned to sinus rhythm within a few minutes.

Implantable cardiac rhythm management (CRM) devices, including pacemakers and implantable cardioverter/defibrillators (ICDs), and have been used to deliver effective treatment to patients with serious cardiac arrhythmias. Cardiac rhythm management devices may treat cardiac arrhythmias with a variety of tiered therapies. These tiered therapies range from delivering low energy pacing pulses timed to assist the heart in maintaining pumping efficiency to providing high energy shocks to terminate fibrillation. To effectively deliver these treatments, the CRM must first identify the type of arrhythmia that is occurring, after which appropriate therapy may be delivered to the heart.

SUMMARY OF THE INVENTION

The present invention is directed to methods and systems for creating and updating cardiac waveform templates representing a number of cardiac waveform morphologies. In accordance with one embodiment of the invention, a method of processing cardiac signals involves providing a template comprising one or more target regions. Each target region is associated with a cardiac waveform feature. A cardiac waveform is detected and features of the cardiac waveform are used to adjust the target regions. The target regions are adjusted based on relationships between the target regions and features of the detected cardiac waveform respectively associated with the target regions.

Another embodiment of the invention involves a method of analyzing cardiac rhythms. The method includes providing one or more templates comprising target regions respectively associated with cardiac waveform features. Cardiac waveforms are detected using the one or more templates.

In accordance with a further embodiment of the invention, a method of generating a cardiac waveform template includes providing target regions, each target region defined by one or more characteristics. A template is established using the target regions.

Another embodiment involves a medical system for processing cardiac signals. The medical system includes a detector system configured to detect cardiac waveforms. The medical system further includes a template processor coupled to the detector system. The template processor is configured to provide one or more templates comprising target regions respectively associated with cardiac waveform features and to adjust the target regions based on relationships between the target regions and associated features of the detected cardiac waveforms.

A further embodiment of the invention is directed to a medical system for processing cardiac waveforms. The medical system includes means for providing a template including target regions, wherein each target region is associated with a cardiac waveform feature, means for detecting a cardiac waveform and means for adjusting the target regions based on relationships between the target regions and features of the detected cardiac waveform respectively associated with the target regions.

In a further embodiment of the invention, a medical system for analyzing cardiac waveforms includes means for providing one or more templates. The templates include target regions respectively associated with cardiac waveform features. The medical system also includes means for analyzing detected cardiac waveforms using the one or more templates.

Another embodiment is directed to a medical system for generating a cardiac waveform template including means for providing target regions. Each target region is defined by one or more characteristics. The medical system further includes means for establishing a template using the target regions.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
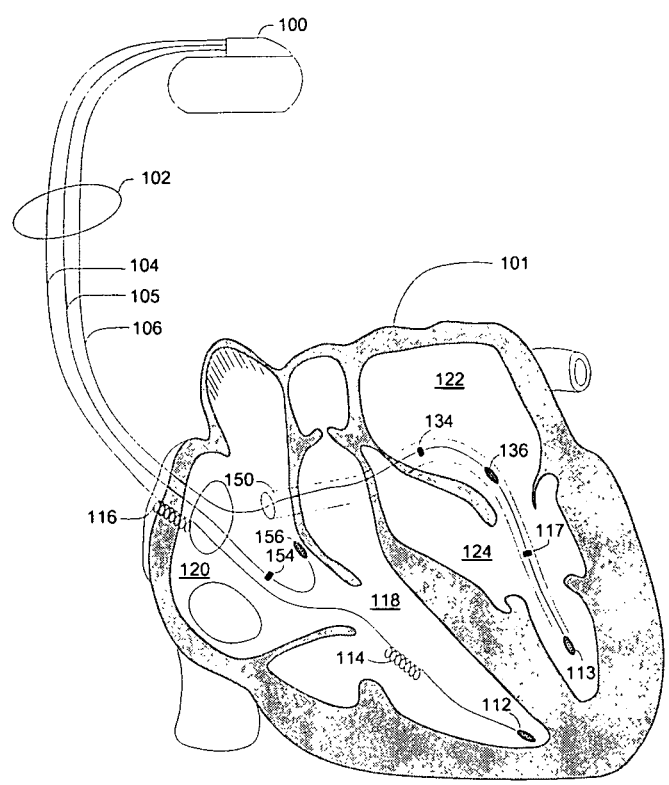
FIG. 1 is a partial view of one embodiment of an implantable medical device that may be used to implement cardiac template creation and maintenance in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Cardiac beats may be analyzed by examining the morphology of the electrical cardiac signal waveform. For example, a cardiac beat may be classified as a normal beat, e.g., a normally conducted supraventricular rhythm, by comparing the cardiac signal waveform to a template characterizing a normal beat. If the cardiac signal waveform is consistent with the template, the cardiac beat may be classified as normal. Similarly, a sensed abnormal or arrhythmic cardiac beat may be classified by comparing the abnormal cardiac signal waveform to one or more templates. The beat may be classified as abnormal if the beat waveform does not match a normal beat template. Such comparisons may be used to determine that the sensed cardiac beat is abnormal as well as to assess the type of abnormality.

According to embodiments of the invention, a cardiac waveform template may be created and used to analyze or otherwise process a sensed cardiac signal for a variety of purposes, including, for example, arrhythmia prediction or detection, as well as analysis of various attributes of the sensed cardiac signal, such as changes in QRS width, T-wave amplitude, Q-wave amplitude or QT interval. A cardiac waveform template may be formed, for example, by identifying one or more cardiac waveform features representative of a particular cardiac beat morphology The particular waveform features may include morphological features such as critical points, significant points, curvature, local extrema, inflection points, rise or fall times, slopes, or the like.

Target regions associated with the identified cardiac waveform features may be defined. One or more target regions may be used to establish a template representing a particular waveform morphology, such as a normally conducted cardiac rhythm, an arrhythmogenic beat, or captured beat, for example. A cardiac waveform may be classified as matching the template if a selected number of the cardiac waveform features fall within the target regions of the template.

In accordance with embodiments of the invention, creation of a template comprising one or more target regions may be followed by adjustment of the template. Adjustment of a template may be necessary to accommodate gradual changes in cardiac beat morphology over time. According to embodiments of the invention, a target region of a template may be adjusted based on a relationship between a current location of the associated cardiac waveform feature and the previous configuration of the target region.

Embodiments of the present system illustrated herein are generally described as being implemented in an implantable cardioverter/defibrillator (ICD), which may operate in numerous cardioversion/defibrillation and pacing modes known in the art. Various types of single and multiple chamber ICDs may be used to implement a number of pacing therapies as are known in the art, in addition to cardioversion/defibrillation therapies. An ICD may implement various anti-tachyarrhythmia therapies, such as tiered anti-tachyarrhythmia therapies, which may involve performing rate-based and/or morphological tachyarrhythmia discrimination analyses.

It is understood that configurations, features, and combination of features described in the instant disclosure can be implemented in a wide range of implantable or external medical devices, and that such embodiments and features are not limited to the particular devices described herein. The systems and methods described herein may be implemented in a wide variety of implantable or external diagnostic and/or therapeutic cardiac devices such as defibrillators, cardioverters, pacemakers, cardiac monitors, and resynchronizers, for example.

Furthermore, although the present system is described in conjunction with an implantable cardioverter/defibrillator (ICD) having a microprocessor-based architecture, it will be understood that the cardiac rhythm management system may be implemented in any logic-based integrated circuit architecture, if desired.

In one embodiment, the cardiac rhythm management system is an implantable cardioverter/defibrillator configured as a single chamber device that operates to process cardiac waveforms according to a template methodology in accordance with the principles of the present invention. In another embodiment, the cardiac rhythm management system is an implantable cardioverter/defibrillator that is configured as a dual chamber device. In yet another embodiment, the cardiac rhythm management system is an implantable cardioverter/defibrillator configured to sense and/or provide electrical stimulation to multiple heart chambers, for example, both ventricles of the heart, as in a resynchronizer used to treat congestive heart failure (CHF).

Referring now to FIG. 1 of the drawings, there is shown one embodiment of a cardiac rhythm management system which includes an ICD 100 electrically and physically coupled to an intracardiac lead system 102. The intracardiac lead system 102 is implanted in a human body with portions of the intracardiac lead system 102 inserted into a heart 101. The intracardiac lead system 102 is used to detect electric cardiac signals produced by the heart 101 and to provide electrical energy to the heart 101 under certain predetermined conditions to treat cardiac arrhythmias.

The intracardiac lead system 102 includes one or more electrodes used for pacing, sensing, and/or defibrillation. In the particular embodiment shown in FIG. 1, the intracardiac lead system 102 includes a right ventricular lead system 104, a right atrial lead system 105, and a left atrial/ventricular lead system 106. In one embodiment, the right ventricular lead system 104 is configured as an integrated bipolar pace/shock lead.

The right ventricular lead system 104 includes an SVC-coil 116, an RV-coil 114, and an RV-tip electrode 112. The RV-coil 114, which may alternatively be configured as an RV-ring electrode, is spaced apart from the RV-tip electrode 112, which is a pacing electrode for the right ventricle.

The right atrial lead system 105 includes a RA-tip electrode 156 and an RA-ring electrode 154. The RA-tip 156 and RA-ring 154 electrodes may provide pacing pulses to the right atrium of the heart and may also be used to detect cardiac signals from the right atrium. In one configuration, the right atrial lead system 105 is configured as a J-lead.

In this configuration, the intracardiac lead system 102 is shown positioned within the heart 101, with the right ventricular lead system 104 extending through the right atrium 120 and into the right ventricle 118. In particular, the RV-tip electrode 112 and RV-coil electrode 114 are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

An LV-tip electrode 113, and an LV-ring electrode 117 are inserted through the coronary venous system and positioned adjacent to the left ventricle 124 of the heart 101. The LV-ring electrode 117 is spaced apart from the LV-tip electrode, 113 which is a pacing electrode for the left ventricle. The LV-tip 113 and LV-ring 117 electrodes may also be used for sensing the left ventricle. The left atrial/left ventricular lead system 106 further includes an LA-tip 136 and LA-ring 134 electrode positioned adjacent the left atrium 122 for pacing and sensing the left atrium 122 of the heart 101.

The left atrial/left ventricular lead system 106 includes endocardial pacing leads that are advanced through the superior vena cava (SVC), the right atrium 120, the valve of the coronary sinus, and the coronary sinus 150 to locate the LA-tip 136, LA-ring 134, LV-tip 113 and LV-ring 117 electrodes at appropriate locations adjacent to the left atrium and ventricle 122, 124, respectively.

The left atrial/left ventricular lead 106 is guided into the right atrium 120 of the heart via the superior vena cava. From the right atrium 120, the left atrial/left ventricular lead system 106 is deployed into the coronary sinus ostium, the opening of the coronary sinus 150. The lead system 106 is guided through the coronary sinus 150 to a coronary vein of the left ventricle 124. This vein is used as an access pathway for leads to reach the surfaces of the left atrium 122 and the left ventricle 124 which are not directly accessible from the right side of the heart. Lead placement for the left atrial/left ventricular lead system 106 may be achieved via subclavian vein access and a preformed guiding catheter for insertion of the LV and LA electrodes 113, 117, 136, 134 adjacent the left ventricle 124 and left atrium 122, respectively. In one configuration, the left atrial/left ventricular lead system 106 is implemented as a single-pass lead.

Figure 2:
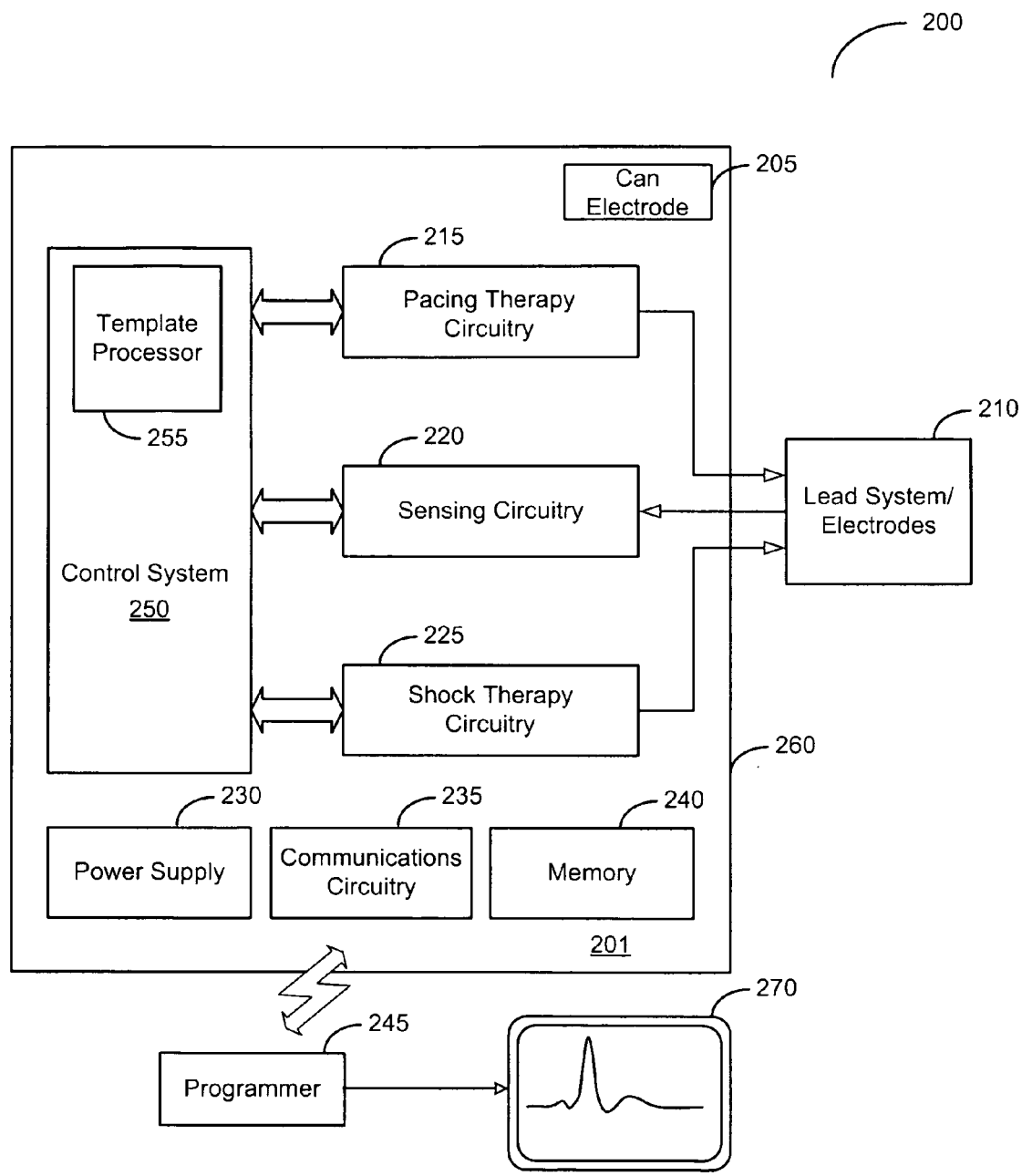
FIG. 2 is a block diagram illustrating functional components of an implantable medical device with which template creation and template adjustment methods may be implemented in accordance with embodiments of the present invention.

Referring now to FIG. 2, there is shown an embodiment of a CRM system 200 employing an ICD 260 suitable for implementing a template creation and adjustment methodology of the present invention. FIG. 2 shows the CRM system 200 divided into functional blocks. There exist many possible configurations in which these functional blocks can be arranged. The example depicted in FIG. 2 is one possible functional arrangement. The CRM system 200 includes circuitry for receiving cardiac signals from a heart and delivering electrical energy in the form of pace pulses or cardioversion/defibrillation pulses to the heart.

A cardiac lead system 210 may be implanted so that cardiac electrodes contact heart tissue as described above in connection with FIG. 1. The cardiac electrodes of the lead system 210 sense cardiac signals associated with electrical activity of the heart. The sensed cardiac signals may be transmitted to an ICD 260 through the lead system 210. The cardiac electrodes and lead system 210 may be used to deliver electrical stimulation generated by the ICD 260 to the heart to mitigate various cardiac arrhythmias. The ICD 260, in combination with the cardiac electrodes and lead system 210, may detect cardiac signals and deliver therapeutic electrical stimulation to any of the left and right ventricles and left and right atria, for example. A can electrode 205 coupled to a housing of the ICD 260 may additionally be used to sense cardiac signals and deliver electrical stimulation to the heart.

In one embodiment, ICD circuitry 201 is encased in a hermetically sealed housing suitable for implanting in a human body. Power is supplied by an electrochemical battery 230 that is housed within the ICD 260. In one embodiment, the ICD circuitry 201 is a programmable microprocessor-based system, including a control system 250, sensing circuit 220, pacing therapy circuit 215, shock therapy circuit 225, and memory 240. The memory 240 may be used, for example, to store template information, parameters for various pacing, defibrillation, and sensing modes, and data associated with sensed cardiac signals or other information. The parameters and data stored in the memory 240 may be used on-board for various purposes and/or transmitted via telemetry to an external programmer unit 245, as required.

The control system 250 may used to control various subsystems of the ICD 260, including the pacing therapy circuit 215, the shock therapy circuitry 225, and the sensing circuitry 220. The control system 250 may also include a template processor 255 for implementing a template methodology according to embodiments of the invention.

Communications circuitry 235 allows the ICD 260 to communicate with an external programmer unit 245. In one embodiment, the communications circuitry 235 and the programmer unit 245 use a wire loop antenna and a radio frequency telemetric link to receive and transmit signals and data between the programmer 245 and communications circuitry 235. In this manner, programming commands may be transferred to the ICD 260 from the programmer 245 during and after implant. In addition, stored cardiac data may be transferred to the programmer unit 245 from the ICD 260, for example.

Sensing circuitry 220 detects cardiac signals sensed at the cardiac electrodes 210. The sensing circuitry may include, for example, amplifiers, filters, A/D converters and other signal processing circuitry. Cardiac signals processed by the sensing circuitry may be communicated the control system 250 and to the template processor 255.

The control system 250 is coupled to the template processor 255 and uses templates created and maintained by the template processor 255 to perform various functions, including, for example, arrhythmia analysis. An arrhythmia analysis section of the control system 250 may compare cardiac signals detected through the sensing circuitry 220 to the templates created and maintained by the template processor 255 to detect or predict various cardiac arrhythmias.

The pacing therapy circuit 215 is controlled by a pacemaker in the control system 250 and may be used to deliver pacing stimulation pulses to the heart through one or more of the cardiac electrodes, according to a pre-established pacing regimen under appropriate conditions. The shock therapy circuit 225 is coupled to an arrhythmia analysis section of the control system 250 and may be used to deliver high energy electrical stimulation to the heart to terminate or mitigate cardiac arrhythmias such as atrial or ventricular tachycardia or fibrillation detected or predicted by the control system 250.

The ICD 260 may optionally be coupled to a display device 270 capable of displaying various information related to template creation and maintenance, and/or cardiac rhythm analysis using morphological templates, as well as other information. For example, the display device 270 may depict a graphical display of one or more detected cardiac waveforms along with the templates used to analyze or classify the detected cardiac waveforms. The display may show various data regarding the number of templates used by the ICD, including, for example, statistics relating to the frequency particular templates were used to analyze or classify cardiac waveforms. Other uses for the display in connection with the template creation and adjustment methods of the invention are also possible.

Figure 3:
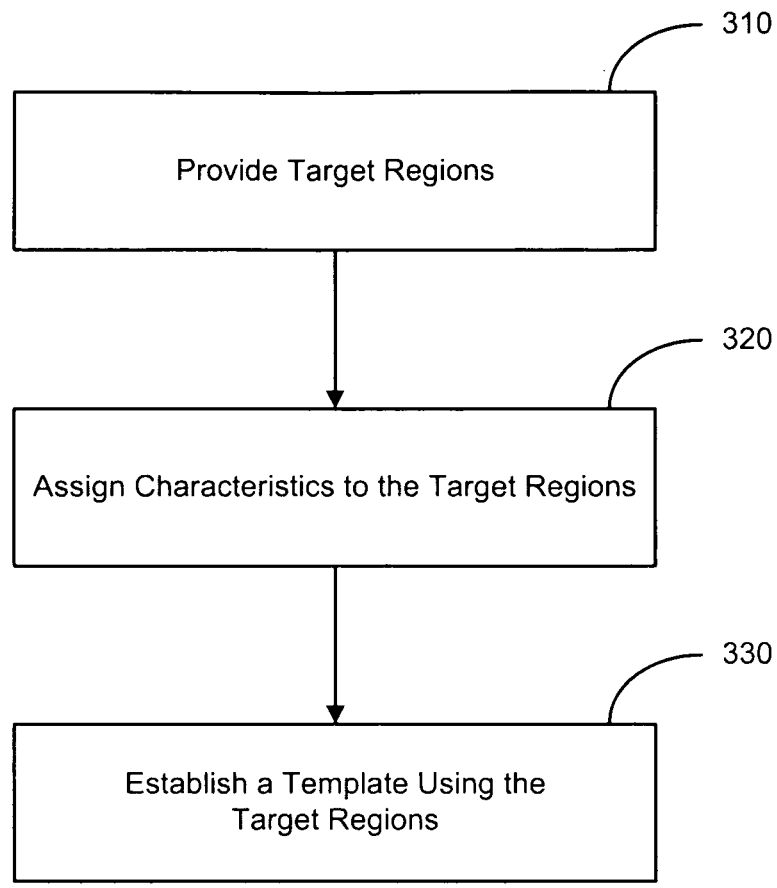
FIG. 3 is a flowchart of a method of creating a cardiac waveform template in accordance with embodiments of the present invention.

The template processor 255, in cooperation with other ICD components, is primarily responsible for implementing template creation and maintenance methods according to embodiments of the present invention. A template creation method according to embodiments of the invention is illustrated in FIGS. 3-6. FIG. 3 provides a flowchart of a template creation methodology. The creation of a cardiac waveform template involves providing 310 target regions and assigning or otherwise relating to the target regions one or more characteristics. Characteristics of a target region may include, for example, attributes such as location, size, and shape of the target region. Target region characteristics may also comprise attributes related to a type of cardiac waveform feature associated with the target region, including, for example, inflection direction (up/down) or sampling rate (fast/slow). A template is established 330 using the target regions.

Figure 4:
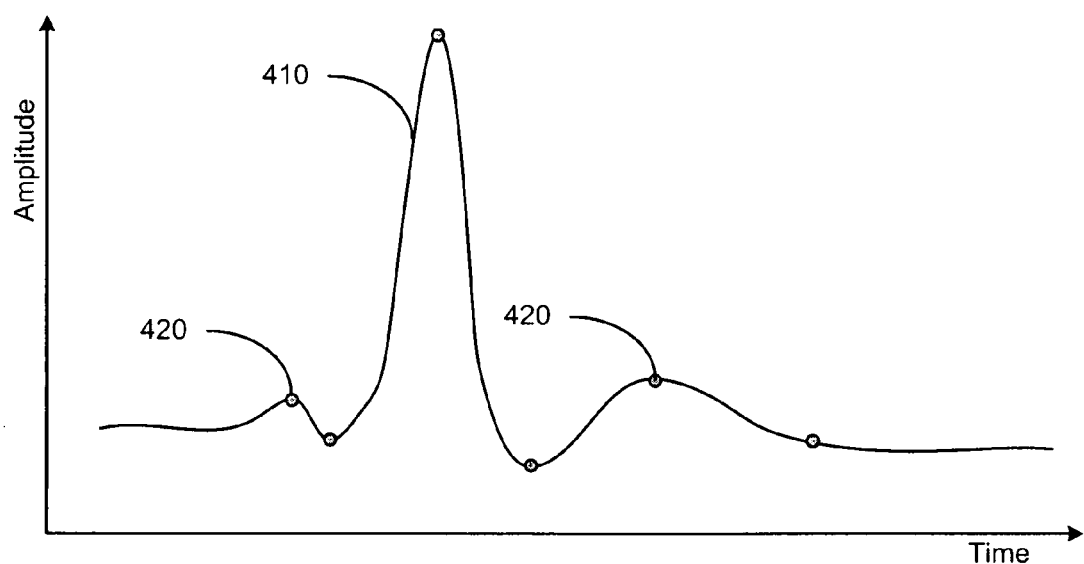
FIG. 4 is a graph illustrating a cardiac signal having cardiac waveform features in accordance with embodiments of the invention.
Figure 5:
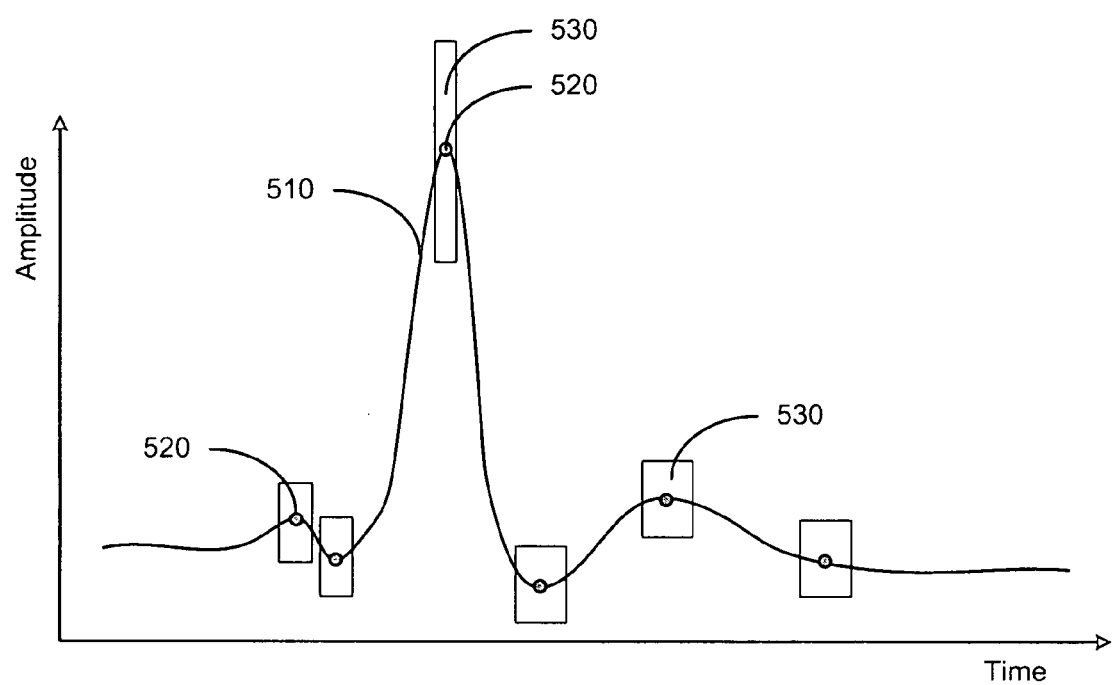
FIG. 5 is a graph illustrating target regions associated with cardiac waveform features in accordance with embodiments of the invention.
Figure 6:
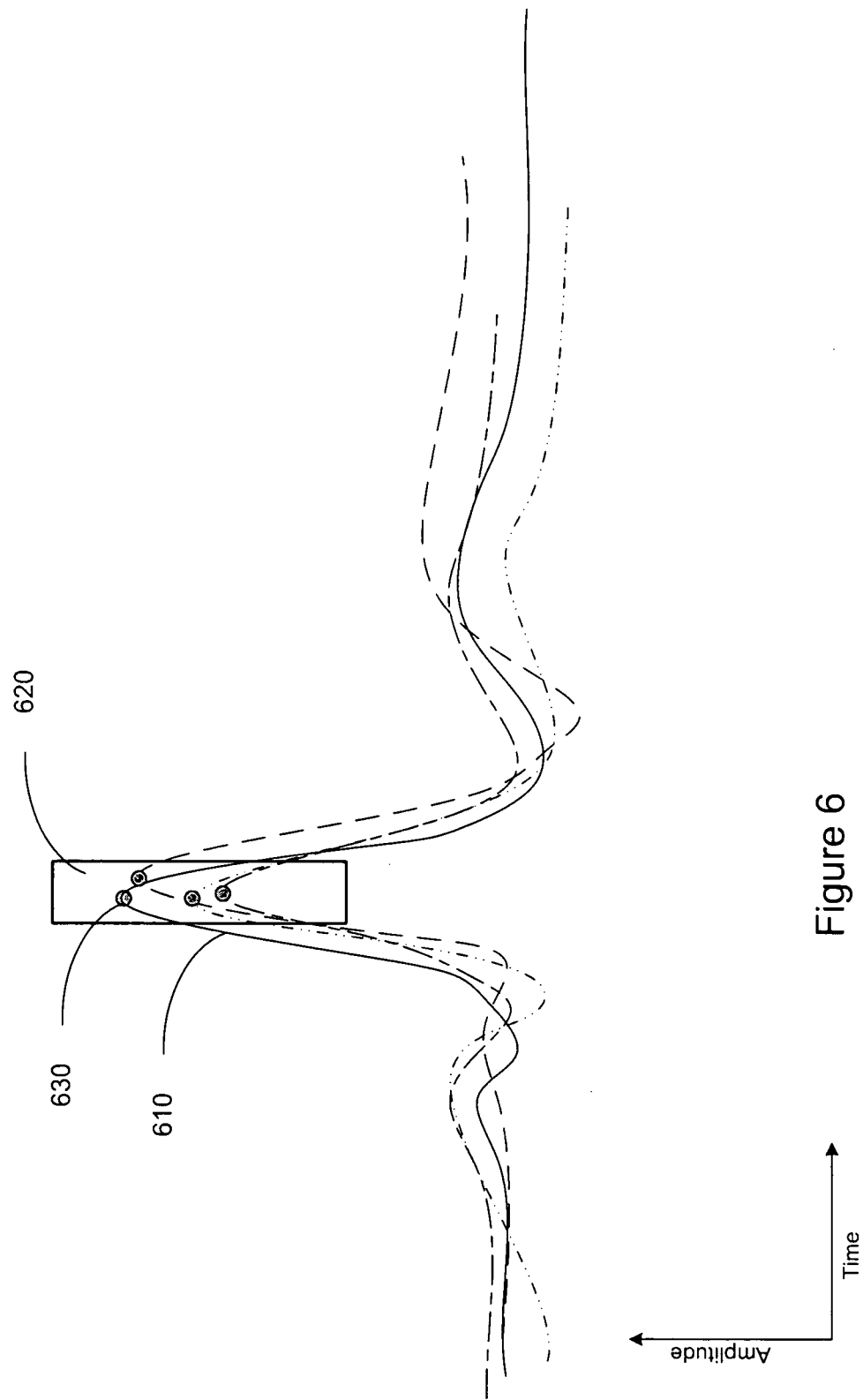
FIG. 6 is a graph illustrating establishment of a target region based on cardiac waveform features detected in multiple cardiac signals in accordance with embodiments of the present invention.

FIGS. 4-6 illustrate a process of creating a template characterizing a particular beat morphology in accordance with embodiments of the invention. The template may include one or more target regions characterizing a cardiac waveform representative of the particular beat morphology, for example.

As illustrated in FIG. 4, a cardiac waveform 410 representing a particular beat morphology is sensed and occurrences of one or more cardiac waveform features 420 are detected. A waveform feature 420 may include a particular point of a cardiac signal waveform 410. The waveform features 420 may be identified based on various morphological aspects of the cardiac waveform, such as critical points, local extrema, inflection points, or by other aspects.

Turning to FIG. 5, a target region 530 may be associated with occurrences of a cardiac waveform feature 520. Each of target regions 530 of a template are defined by a particular size, shape, and location. The cardiac waveform features 520 and the associated target regions 530 may also be assigned additional attributes. For example, a cardiac waveform feature 520 and associated target region 530 may be associated with a positive or negative inflection direction of the cardiac waveform 510 at the waveform feature point 520. Thus, a target region 530 may be defined using various amplitude and time coordinates to identify the size, shape, and location of the target region, and may also be assigned additional attributes, such as positive or negative inflection.

In accordance with embodiments of the invention, a target region 530 associated with a waveform feature 520 may also be classified with respect to the sampling rate used to detect the waveform feature 520. For example, target regions 530 may be considered to represent "fast" features or "slow" features based on the sampling rate used to detect the waveform feature 520. If a relatively slow sampling rate is used to detect the waveform feature 520, then the respective target region 530 is associated with a slow feature point. If a relatively high sampling rate is used to detect the waveform feature 520, e.g., about 4 times the slow sampling rate, then the respective target region 530 is associated with a fast feature point. A faster sampling rate may be used, for example, to detect a waveform feature exhibiting a high rate of change, such as the peak of an R-wave. A slower sampling rate may be useful in more accurately detecting a slowly varying waveform feature, such as the T-wave, for example.

FIG. 6 illustrates a process for defining a target region associated with a particular cardiac waveform features. As previously discussed, one or more target regions may be used to establish a template representing a particular beat morphology. As illustrated in FIG. 6, a number of cardiac signal waveforms 610 representative of a particular cardiac beat morphology may be acquired and used to establish a template, in accordance with embodiments of the invention. One or more cardiac waveform features 630 are detected for each of the cardiac waveforms 610. In this example, the detected cardiac waveform features 620 represent a maximum value of the cardiac waveform 610. A maximum value for each cardiac waveform is defined in terms of amplitude and time coordinates. A target region 630 associated with the maximum value of the cardiac waveform for the particular beat morphology may be defined by various methods. According to various embodiments, a target region 630 for a particular waveform feature 62, e.g., maximum value, may be established so that the target region 630 encloses all the feature points 620 of the respective cardiac waveforms 610. In this example, the size (area) and the shape of the target region may be dynamically determined by the waveform feature points used to establish the target region.

In another embodiment, the target region 630 may be established based on an average of the feature coordinates for each cardiac waveform. The average of the detected waveform feature coordinates may be defined as a point, such as a center, or other location, within a target region. In this example, the boundaries of the target region may be established according to a predetermined shape, for example, a circle, square, rectangle, rhombus, or other quadrilateral. Additionally or alternatively, the target region may be created to enclose a predetermined area.

In yet another embodiment, one or more target regions of a template may be defined based on a single cardiac waveform representing the particular beat morphology.

In various embodiments, target regions of a template may initially be defined based on predetermined criteria, and then allowed to dynamically associate with a compatible cardiac waveform feature. In accordance with this embodiment, one or more target regions of a template may be assigned predetermined criteria with respect to area, size, location, inflection, and fast/slow sampling rate, for example. The predetermined criteria may be established by various techniques. For example, the predetermined criteria may be pre-programmed, or may be programmable by a physician. The target regions may then be allowed to "find" compatible cardiac waveform features in a detected cardiac waveform in accordance with the template/target region adjustment methods described below.

Other methods of establishing a cardiac waveform template based on one or more target regions are also possible and are within the scope of the invention. Regardless of the initial method used to create a template, the target regions of a template may be adjusted using cardiac waveform features of subsequently detected beats having a similar morphology.

Figure 7:
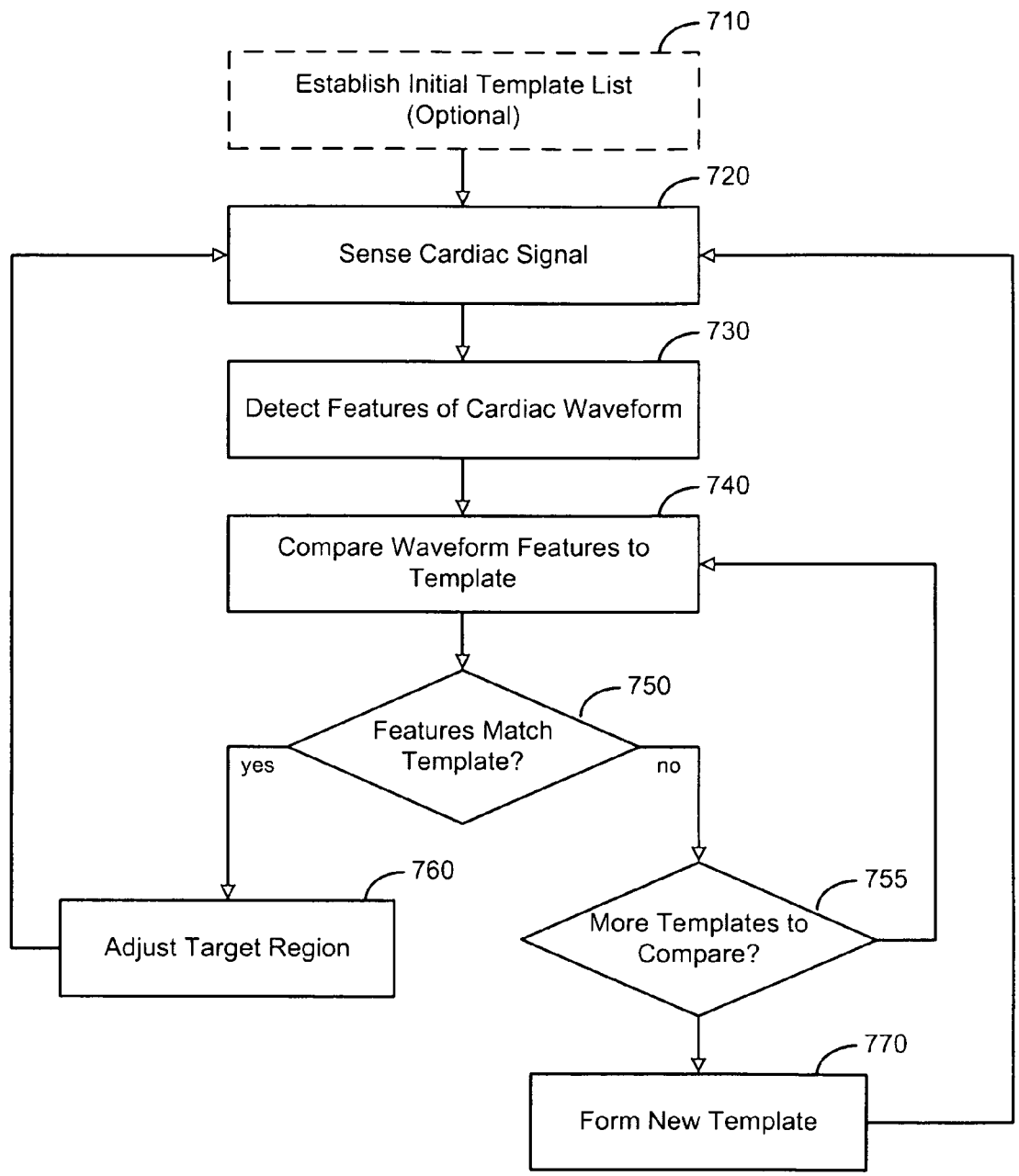
FIG. 7 is a flow chart illustrating a method of creating a template using target regions in accordance with embodiments of the invention.

FIG. 7 is a flowchart illustrating a method of automatic template creation according to embodiments of the invention. According to this embodiment, an initial template list comprising a list of templates representative of various cardiac beat morphologies may optionally be established 710. Alternatively, new templates may be formed without an initial template list using the processes described below. A cardiac signal is sensed 720. The waveform features of the cardiac signal are detected 730 and compared 740 to each template in the template list, if any. If a predetermined number of the detected features of the cardiac waveform fall within the target regions of the template, e.g., six of seven cardiac waveform features fall within target regions of the template, the cardiac waveform may be classified as matching 750 the template. The template may optionally be adjusted 760 using the detected cardiac waveform features. Example methods for adjusting the template are described in more detail below.

If the detected waveform features do not match 750 a template, the waveform features are compared to the next template until all templates have been compared 755 to the cardiac waveform features. If none 755 of the templates match the cardiac waveform features, a new template may be created 770 by defining target regions associated with the detected waveform features.

A cardiac signal waveform may exhibit natural variations in its morphology over time. Unless a template is adjusted periodically, the cardiac waveform morphology may gradually drift away from the originally established template. It may be desirable to adjust the template to track changes in the cardiac waveform.

Figure 8:
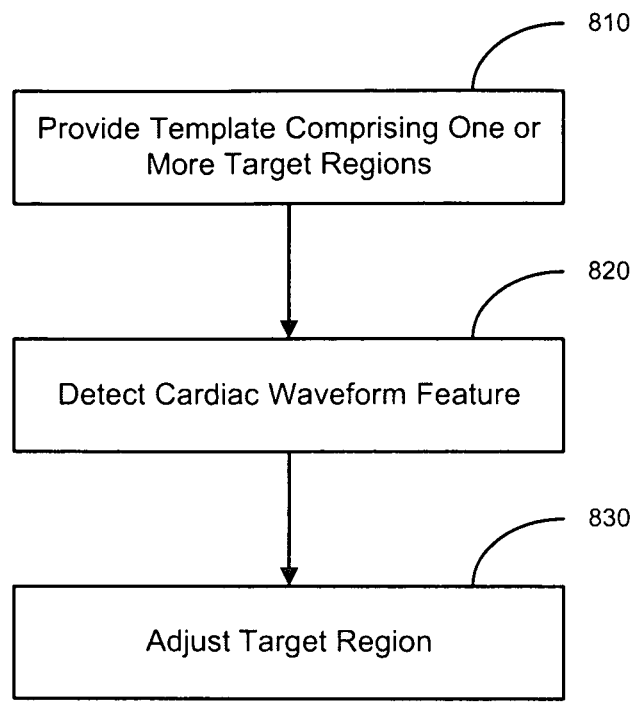
FIG. 8 is a flow chart illustrating a method of adjusting a target region in accordance with embodiments of the invention.

The flowchart of FIG. 8 illustrates a method of adjusting a template in accordance with embodiments of the invention. According to this method, a template comprising at least one target region is provided 810. The template may include one or more target regions associated with cardiac waveform features and defined according to processes described above. Alternatively, the template may include target regions defined using predetermined criteria. In this situation, the target regions are allowed to migrate toward and eventually become associated with cardiac waveform features consistent with the attributes of the target regions.

A cardiac signal is sensed and one or more features of the cardiac waveform are detected 820. The template is adjusted 830 by modifying one or more target regions of the template based on a relationship between the target regions and the associated cardiac waveform features detected in the cardiac waveform.

In accordance with embodiments of the invention, a template may be adapted to changes in cardiac waveform morphology by adjusting one or more target regions of the template. A particular target region may be adjusted according to a relationship, e.g., a spatial relationship, between the particular target region and its associated waveform feature. Adjustment of the target regions of a template may involve, for example changing the size, shape, or location of the target region.

A cardiac feature location may be identified by a timing coordinate (usually represented as the x-axis) and an amplitude coordinate (y-axis). A target region may be adjusted based on a relationship between a detected feature's amplitude coordinate and the associated target region's amplitude range. A target region may also be adjusted based on a relationship between an associated detected feature's timing coordinate and the target regions amplitude range. In other examples, the target region may be adjusted based on a variability of an associated detected feature's timing and/or amplitude coordinates.

According to embodiments of the invention, the adjustment of a target region involves modifying the target region in the direction of an associated cardiac feature location. In various examples, a detected cardiac feature may fall within a particular template region, but be offset from the center of the target region. The location, size, and/or shape of the target region may be modified in the direction of re-centering or otherwise re-orienting the target region with respect to an associated detected cardiac feature point falling within the target region. The target region may be adjusted using a function-based or rules-based technique.

According to one implementation, adjustment of the target regions may be accomplished using a function that is based on present and past locations of an associated detected cardiac waveform feature. According to one example, the target region may be adjusted using an exponential average based on the present location of the waveform feature and the previous locations of the target region. Adjustment of the target region may implemented based on Equation 1 below.

$$\text{Adjusted Location} = \forall * \text{Past Location} + (1-\forall) * \text{Current Location} \quad [1]$$

By setting the values of $\forall$, more emphasis may be placed on the past location of the target region, corresponding to $\forall > 0.5$, or more emphasis may be placed on the current location, corresponding to $\forall < 0.5$. The location of the target region may be determined by re-centering or otherwise re-orienting the target region using the adjusted location.

A target region may be adjusted using a rules-based technique. For example, the target region may be adjusted in the direction of a detected associated feature point based on one or more re-centering rules.

A cardiac beat may be required to meet certain qualifications before it is used to adjust the target regions of a template. A cardiac beat qualified to update a template may be required to meet certain timing, rate, amplitude, regularity, or other criteria. For example, a qualified cardiac beat used to update a normal waveform template may be required to have one or more characteristics, e.g., the beat and one or more previous cardiac beats may be required to be intrinsic beats, to be associated with a heart rate less than a predetermined value, and to have a signal peak less than a predetermined amount.

Figure 9B:
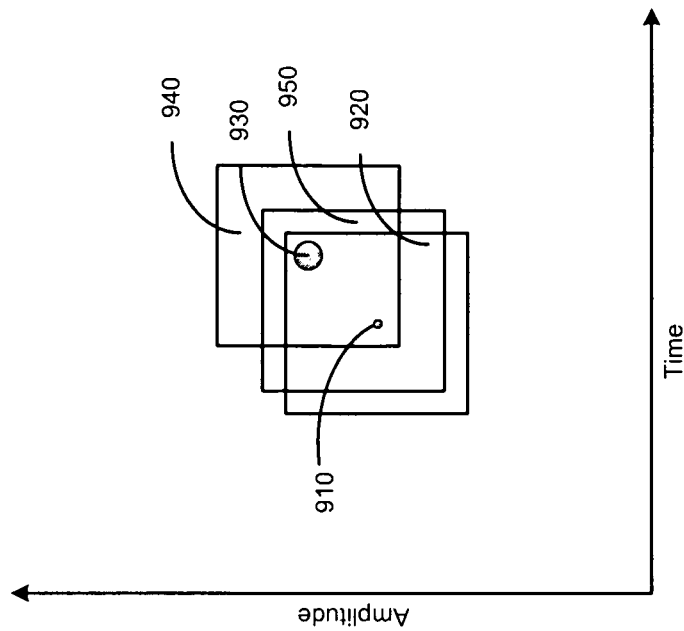
FIGS. 9A-B are diagrams illustrating a process of adjusting the location of a target region in accordance with embodiments of the invention.
Figure 9A:
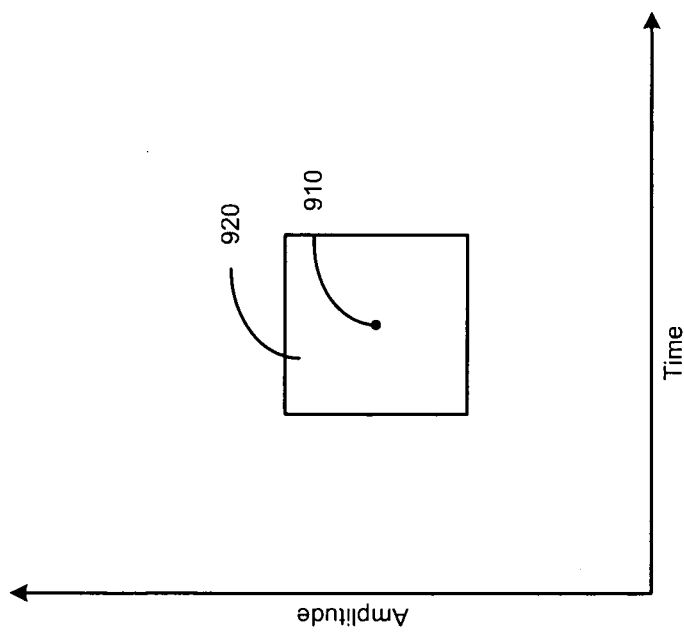

Adjustment of a target region is illustrated in the diagrams of FIGS. 9A-B. FIG. 9A illustrates a target region 920 having a center 910 based on locations of the previously detected cardiac waveform features associated with the target region. FIG. 9B illustrates the situation after the next cardiac signal is sensed. The current cardiac waveform feature point 930 is detected. The location of the current feature point 930 has drifted above and to the right of the original center 910 illustrated in FIG. 9A. A current target region 940 centered on the new cardiac waveform feature 930 would represent a significant change from the original target region 920. In one example embodiment, adjustment of the target region is performed so that beat-to-beat modifications exhibit a relatively smooth transition. The adjusted target region 950 may be determined, for example using Equation 1 or other method, to smoothly accommodate the waveform feature drift based on both the past target region location 920 and the current target region location 940. The adjustment of the target region may be limited to predetermined upper and lower boundaries with respect to the amplitude and time coordinates.

Although Equation 1 mathematically describes adjusting the target region location using an exponential average, other methods of adjusting the target region locations are also possible. For example, in other embodiments, each of the one or more target regions in a template may be adjusted according to a moving window average, or another function representing the change in distance between the original target region and the waveform feature. In a further embodiment, the target regions may be adjusted according to a rules-based process. A rules-based adjustment process may involve adjusting the target region location by an amount based on the locations of subsequently detected cardiac waveform features. For example, the target region location may be moved an incremental amount to the right if a predetermined number, e.g., five, consecutive cardiac signals exhibit cardiac waveform features located within the target region, but to the right of center of the original target region. Adjustments in other directions, i.e, left, up, and down, may be made using similar criteria.

Figure 9D:
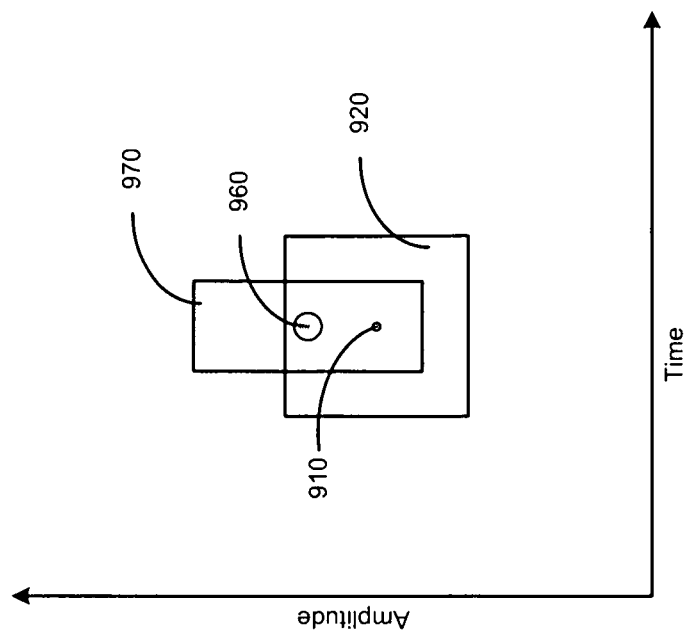
FIGS. 9C-D are diagrams illustrating a process of adjusting the shape of a target region in accordance with embodiments of the invention.
Figure 9C:
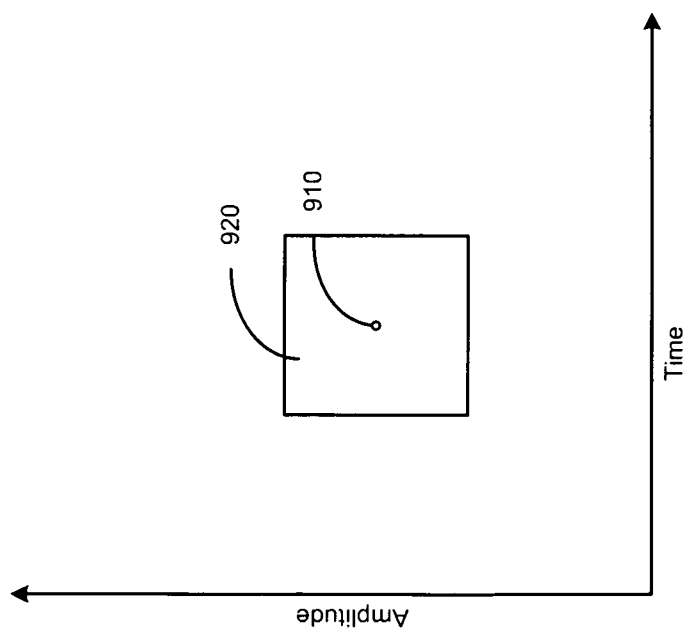

In yet other embodiments, adjustment of the target region may include adjusting the shape and/or size of the target region. FIGS. 9C-D are diagrams illustrating adjusting a target region by modifying the shape of the target region. FIG. 9C illustrates a target region 920 having a center 910. FIG. 9D illustrates the situation after the next cardiac signal is sensed. The cardiac waveform feature 960 associated with the target region 920 is detected. The location of the current feature point 960 has drifted above the original center 910 of the target region 920. An adjusted target region 970, having a different shape from the original target region 920, is defined. The adjustment of the target region may be limited to a predetermined range with respect to the amplitude and time coordinates.

Template adjustment techniques according to embodiments of the invention allow the target regions to track changes of associated cardiac waveform features so long as the changes do not occur too quickly. For example, in the case of template adjustment through exponential averaging, a target region may track changes in the associated cardiac waveform feature if the changes do not occur faster than the exponential decay rate. However, if the location of the cardiac waveform feature moves relatively quickly so that the location falls outside the target region, adaptation may not occur because the target region is unable to track the new location of the cardiac waveform feature. This situation complicates morphology tracking. If the waveform feature falls outside the target region for several beats, the target region may become "lost" until a cardiac signal includes a waveform feature that happens to fall within the target region. If a target region consistently loses track of its associated waveform feature, the morphology of the cardiac waveform may no longer be reliably tracked.

Figure 10A:
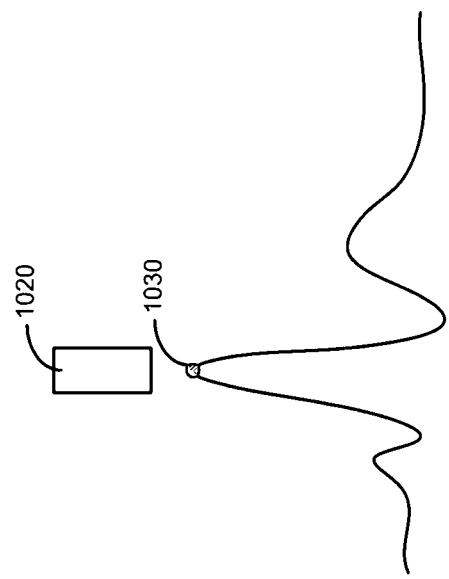
FIGS. 10A-B are diagrams illustrating a "lost" target region in accordance with embodiments of the invention.
Figure 10B:
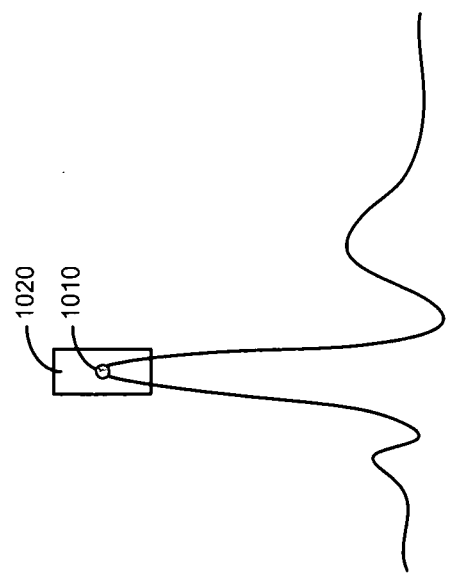

The problem with the "lost" target region situation caused by an out-of-region waveform feature is illustrated in the diagrams of FIGS. 10A-B. The cardiac waveform illustrated in FIG. 10A may persist for a number of beats. In this diagram, the peak of the QRS waveform is defined as a cardiac waveform feature 1010 tracked by an associated target region 1020. For a number of beats, the associated cardiac waveform feature 1010 falls within the target region 1020 and the target region 1020 is able to track the associated cardiac waveform feature 1010.

However, if the next beat has a lower amplitude R peak, the target region 1020 is unable to track the associated cardiac waveform feature 1030, as illustrated in FIG. 10B. In FIG. 10B, the cardiac waveform feature 1030 falls beyond the target region 1020. If the lower R peak persists, the target region 1020 may permanently lose track of the associated cardiac waveform feature 1030.

According to one embodiment, a method for adjusting the target region involves using a nearest appropriate cardiac waveform feature to guide a lost target region back to the cardiac waveform feature. In this embodiment, the attributes of the cardiac waveform feature are assigned to the target region and may be used to guide the target region back to the associated cardiac waveform feature.

As discussed above, each cardiac waveform feature may be assigned attributes such as speed (fast or slow sampling), and direction (positive or negative inflection). The target region associated with the cardiac waveform feature may also be assigned these attributes. Assigning cardiac waveform feature attributes, such as speed and direction, to a target region enables the target region to track its respective cardiac waveform feature even though the waveform feature falls outside the target region.

If a target region becomes lost, a cardiac waveform feature may be nearby, but has drifted outside the range of the target region. Movement of the target region toward a waveform feature with compatible attributes, i.e., a fast or slow feature, and/or a positive or negative inflection, allows the target region to seek and re-find its associated cardiac waveform feature. If the lost target region cannot re-find the cardiac waveform feature within a few beats, the target region may be ignored or removed from the template. Ignoring or removing a particular target region is an indication that the morphology of the cardiac waveform has significantly changed so that the cardiac waveform feature associated with the particular target region is no longer significant.

According to embodiments of the invention, a lost target region may locate a nearby cardiac waveform feature with similar attributes and migrate toward the nearby cardiac waveform feature. If migration causes a target region to converge on another target region, then the two target regions may be merged. In alternate embodiments, the target region may only be allowed to migrate toward a cardiac waveform feature that is not associated with another target region. Further, the range of movement of the target region may be subject to certain constraints. For example, movement of the target region in the amplitude direction (y-axis) and the timing direction (x-axis) may be constrained by an upper and a lower boundary. Further, the target region may not be allowed to move toward a waveform feature point if the waveform feature point is too far away from the location of the target region. Overlapping target regions may also be prohibited. These methods allow a target region to automatically track changes in the beat morphology and to flexibly correct the target region's location when it becomes disassociated from its cardiac waveform feature.

Figure 11:
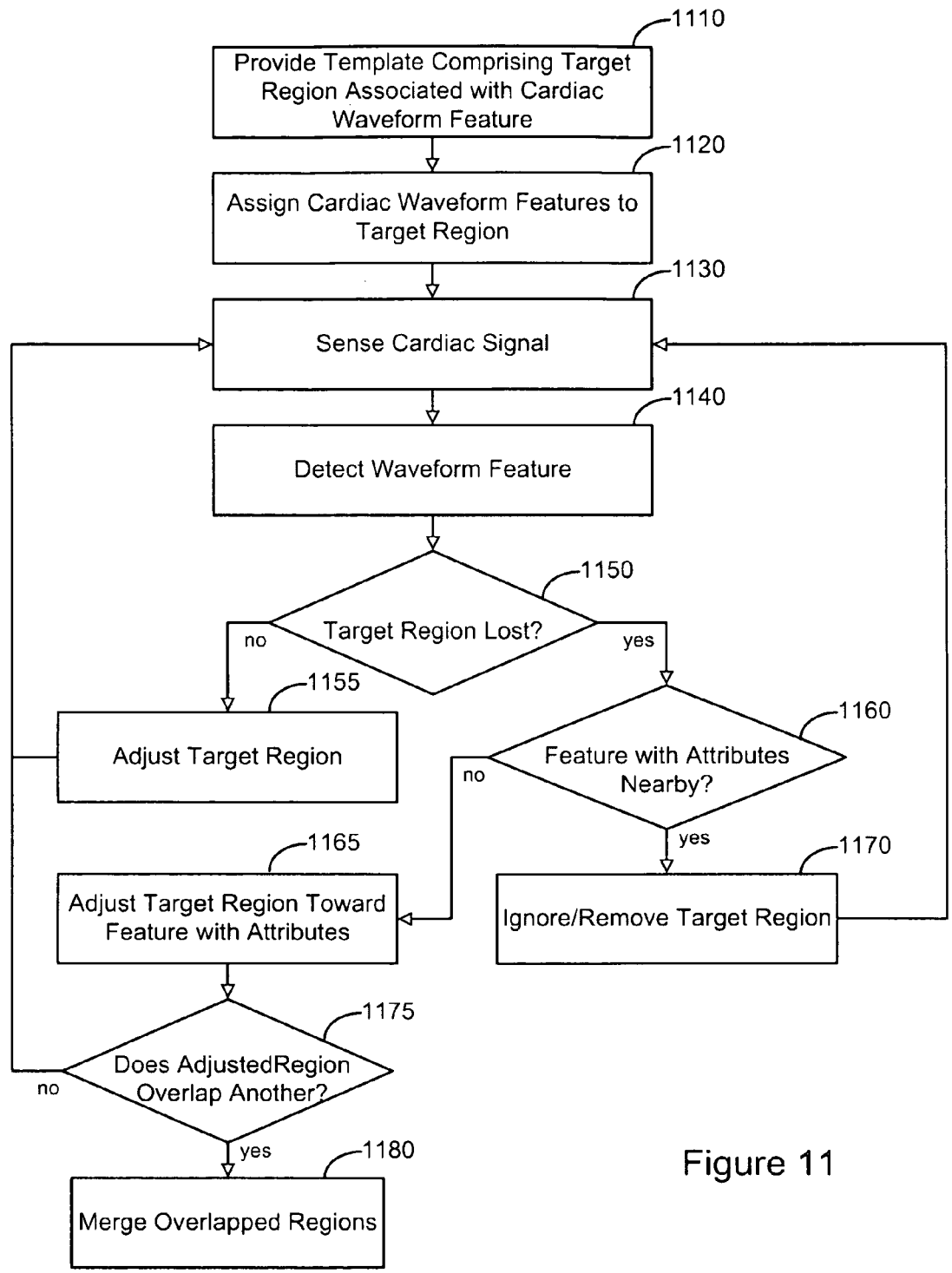
FIG. 11 is a flow chart illustrating a method of adjusting the location of a target region that has become disassociated with a cardiac waveform feature in accordance with embodiments of the invention.

FIG. 11 is a flowchart illustrating a method of adjusting a target region when the cardiac waveform feature associated with the target region repeatedly falls outside the target region. In this situation, as previously discussed, the target region is said to be "lost." Initially, a template is provided 1110 that comprises at least one target region associated with a cardiac waveform feature. The cardiac waveform feature may be assigned one or more attributes, such as sampling rate (fast or slow), and/or inflection direction (up or down). The target region is assigned 1120 the sampling rate and/or inflection direction attributes of the associated cardiac waveform feature. A cardiac signal is sensed 1130 and the cardiac waveform feature detected 1140. If a cardiac waveform feature consistently falls within its target region, the target region is not lost 1150, and the target region may be adjusted 1155 to track changes in the location of the cardiac waveform feature. For example, the center point of the target region may be adjusted towards the location of the detected cardiac waveform feature, such as by the adjustment processes described above. The migration of the target region may be limited to a predetermined range to prevent the target region from wandering far from its original location.

If the cardiac waveform feature consistently falls outside the target region, the target region is lost 1150. The system checks for a nearby cardiac waveform feature that has the same attributes as the target region. If a cardiac waveform feature having the same characteristics as the target region is not located 1160 nearby, then the target region remains lost and the system may eventually ignore the target region or remove 1170 the target region from the template. If a cardiac waveform feature having similar attributes as the target region is located nearby 1160, then the location of the target region is moved toward the nearby cardiac waveform feature 1165 having similar attributes.

Moving a target region toward a nearby cardiac waveform feature with similar attributes may cause the moved target region to overlap an existing target region. If overlap occurs 1175, the overlapped target regions may be merged 1180 into a single target region.

Figure 12B:
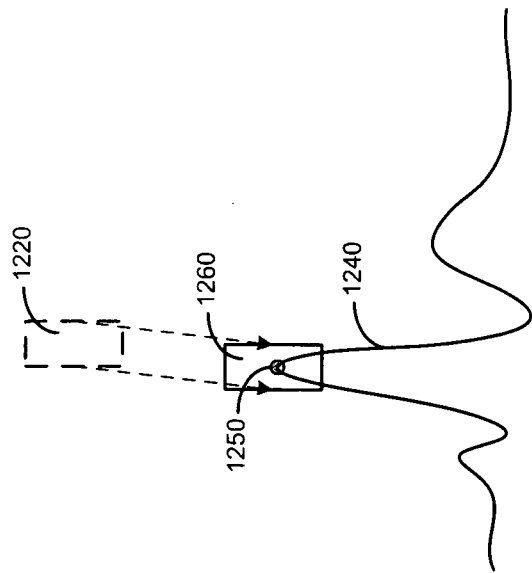
FIGS. 12A-B are graphs illustrating a "lost" target region re-finding its associated cardiac waveform feature in accordance with embodiments of the invention.
Figure 12A:
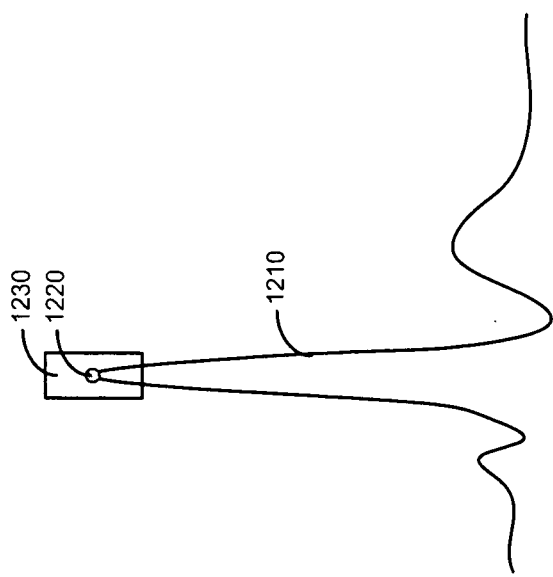

The diagrams of FIGS. 12A-B graphically illustrate the process of adjusting a target region to allow the target region to re-find its associated cardiac waveform feature. FIG. 12A illustrates a cardiac beat 1210 having the QRS peak as a cardiac waveform feature 1220 falling within an associated target region 1230. The diagram of FIG. 12B illustrates a subsequent cardiac beat 1240 having a lower QRS peak. If a sufficient number of cardiac beats exhibit the lower QRS peak, the target region 1260 is allowed to migrate from the original target region location 1220 to assimilate the new location of the cardiac waveform feature 1250.

A template creation process may be based on a similar to method to the target region adjustment method described in connection with FIGS. 11 and 12 according to embodiments of the invention. According to this method, one or more target regions may be assigned predetermined characteristics, e.g., location, size, and shape, and predetermined attributes, e.g., fast/slow and up/down attributes. The target regions so defined represent a particular waveform template. Each target region is then allowed to migrate toward a nearby cardiac waveform feature with matching attributes. As discussed above, if two target regions overlap, and no other cardiac waveform feature with matching characteristics is nearby, then the target regions may be merged. If an appropriate cardiac waveform feature cannot be found for a target region, then the target region may be removed from the template.

The processes described herein may be used to create and adjust cardiac waveform templates representing a variety of cardiac waveform morphologies. Cardiac waveform templates created or adjusting using the methods discussed above may be used to analyze cardiac rhythms. For example, templates representative of one or more types of normal or abnormal cardiac rhythms may be created and stored. The templates may be formed, for example, in response to ICD markers indicating a particular kind of normal or arrhythmic beat. The stored templates may be compared to subsequently detected cardiac signals. If features of a cardiac signal match the template, then the cardiac signal may be classified according to the type of rhythm represented by the matching template. A cardiac signal may be considered to match a template if a predetermined number of cardiac waveform features, e.g., about six of seven cardiac waveform features or about 85% of the cardiac waveform features, fall within target regions of the template. Cardiac templates created and maintained in accordance with embodiments of the invention may be used to classify various normal and abnormal cardiac rhythms, including, for example, normally conducted supraventricular rhythm (NSR), supraventricular tachyarrhythmia (SVT), ventricular tachycardia (VT), and ventricular fibrillation (VF).

In accordance with one embodiment, the template matching process described above may be used in connection with predicting cardiac arrhythmia and triggering the delivery of preventive therapy. In accordance with this embodiment, arrhythmogenic or proarrythmic beats are detected just prior to an arrhythmic episode, e.g., VT or VF episode. The arrhythmogenic waveforms are used to form one or more templates characterizing arrhythmogenic beats. Subsequently detected cardiac signals are compared to the arrhythmogenic templates. The detection of one more of the cardiac signals matching the arrhythmogenic templates may indicate an impending onset of an episode of cardiac arrhythmia. If such a situation occurs, preventive therapy may be applied to prevent the arrhythmia or reduce the severity of the arrhythmia.

Another embodiment of the invention involves using templates created and maintained according to the above described processes in connection with capture verification. This embodiment involves the creation of one or more templates associated with capture verification and comparing the templates with subsequently detected cardiac signals. For example, templates may be created representing a captured waveform, a non-captured waveform, and a fusion waveform. A captured waveform template may be created, for example, by pacing the heart at an energy level in excess of the capture threshold and using one or more evoked cardiac signals to form a captured waveform template. A non-captured waveform may be produced by pacing the heart at an energy level below the capture threshold or during a refractory period. The subsequently detected cardiac waveform may be used to produce a template that represents a non-captured waveform, i.e., the pacing artifact without a superimposed evoked response. Similarly, a fusion waveform template may be generated if ICD markers indicate the occurrence of a fusion beat.

Classification of captured, non-captured and/or fusion beats using target region templates may be used, for example, in connection with a pacing threshold test to determine an optimum pacing energy of a pacemaker. In another example, cardiac waveforms may be compared to a template characterizing a captured or non-captured beat to determine if capture has occurred on a beat-by-beat basis. If capture is not detected, then the pacing energy of the device may be adjusted and/or a back-up pace pulse may be delivered to ensure uninterrupted delivery of pacing therapy.

Target regions created and maintained according to embodiments of the invention may also be used to analyze or monitor changes in various cardiac waveform features. For example, a target region may be compared to a cardiac waveform feature to determine the amount of change occurring in the feature over time. In accordance with this example, a target region corresponding to peak of a cardiac waveform, e.g., R-wave peak, may be compared to one or more subsequently detected cardiac signals to determine an increase or decrease in the R-wave amplitude and/or timing.

In another example of waveform analysis, the QRS width of a cardiac waveform may be analyzed using target regions. In accordance with this example, target regions corresponding to some or all of the Q, R, and S peaks of a particular cardiac waveform morphology may be created. Changes in the QRS widths of subsequently detected cardiac waveforms may be analyzed by comparing the feature points representing the Q, R, and S peaks of the cardiac waveforms to the target regions. It will be appreciated that target regions may be used to analyze and monitor a variety of cardiac waveform morphological features, including, for example, waveform peaks, intervals, and timing. According to embodiments of the invention, a number of templates may be created from cardiac waveform morphologies detected over a predetermined time period of time. The group of templates may be stored and compared to subsequently detected cardiac signals. If the waveform morphology of a detected cardiac signal is consistent with one of the templates, the target regions of the template may be adjusted. If the morphology of the detected cardiac signal does not match any of the stored templates, i.e., the target regions of the stored templates do not match the features of the detected signal, the waveform morphology of the cardiac signal may be used to establish a new template.

A counter or other marker may be used to count the number of times a template has matched the morphology of a cardiac waveform within a time interval. Periodically, the system may delete templates that have fallen into disuse, i.e., the target regions of the templates and have not been matched by a sufficient number of detected cardiac waveform features. For example, templates representing waveform morphologies that have not been detected a sufficient number of times within a predetermined time period, e.g., 30 days, may be deleted. Removal of unused templates prevents the number of stored templates from becoming excessively large.

According to embodiments of the invention, templates created and/or adjusted using the above processes may be used to predict arrhythmias. One or more templates representing arrhythmogenic cardiac waveform morphologies may be established and stored. Subsequently detected cardiac waveforms may be compared to the templates representing arrhythmogenic morphologies. If one or more of the detected cardiac waveforms matches an arrhythmogenic template, the waveform is classified as an arrhythmogenic beat. Classification of one or more beats as arrhythmogenic may trigger delivery of cardiac therapy to prevent arrhythmia.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating an implantable cardiac device comprising:
    associating one or more target region attributes with each of a plurality of target regions, the one or more target region attributes including at least sampling rate and each target region having a location, a time dimension, and an amplitude dimension;
    detecting a cardiac waveform feature;
    adjusting at least one target region of the plurality of target regions based on a location of the detected feature of the cardiac waveform and compatibility between the attributes of the at least one target region and attributes of the waveform feature;
    delivering a cardiac pacing pulse during a cardiac cycle;
    detecting a subsequent cardiac waveform after delivery of the pacing pulse;
    determining a cardiac pacing response to the pacing pulse based on whether features of the subsequent cardiac waveform fall within the plurality of target regions; and
    adjusting a pacing energy of the cardiac device based on the cardiac pacing response.

2. The method of claim 1, wherein adjusting the at least one target region further comprises:
    determining a location of the waveform feature relative to the location of the at least one target region; and
    adjusting the location of the at least one target region toward the location of the waveform feature.

3. The method of claim 1, further comprising:
    determining a location of the waveform feature relative to one or both of the amplitude dimension of the at least one target region and the time dimension of the at least one target region; and
    adjusting one or both of the amplitude dimension of the target region and the time dimension of the target region based on the location of the waveform feature.

4. The method of claim 1, further comprising:
    determining a variability of a location of the waveform feature; and
    adjusting one or both of the amplitude dimension and the time dimension of the at least one target region based on the variability of the location of the waveform feature.

5. The method of claim 1, wherein the features of the cardiac waveform comprise a positive peak and a negative peak.

6. The method of claim 1, wherein:
    the plurality of target regions are associated with a fusion waveform; and
    determining the cardiac pacing response comprises detecting a fusion beat.

7. The method of claim 1, wherein:
    the plurality of target regions are associated with a captured waveform; and
    determining the cardiac pacing response comprises detecting a captured beat.

8. The method of claim 1, wherein adjusting the at least one target region is limited by one or both of a predetermined amplitude boundary and a predetermined time boundary.

9. The method of claim 8, wherein the predetermined amplitude boundary is an upper boundary.

10. The method of claim 8, wherein the predetermined time boundary is a lower boundary.

11. The method of claim 1, wherein adjusting the at least one target region is limited by one or both of a predetermined range of the-time dimension and a predetermined range of the amplitude dimension.

12. An implantable cardiac device, comprising:
    pacing therapy circuitry configured to deliver a pacing pulse to a heart during each of a plurality of cardiac cycles;
    sensing circuitry configured to sense a cardiac waveform after delivery of each pacing pulse; and a control system configured to associate and provide one or more target region attributes with each of a plurality of target regions, the one or more target region attributes including at least sampling rate, each target region having a location, a time dimension, and an amplitude dimension, the control system configured to adjust at least one target region of the plurality of target regions based on a location of at least one sensed cardiac waveform feature and compatibility between attributes of the at least one target region and attributes of the at least one sensed cardiac waveform feature, the control system configured to, for a subsequent cardiac cycle, determine if features of a subsequently sensed cardiac waveform fall within the plurality of target regions and to determine the cardiac pacing response based on whether the cardiac waveform features of the subsequently sensed cardiac waveform fall within the plurality of target regions.

13. The device of claim 12, wherein the control system is configured to detect fusion based on whether the cardiac waveform features of the subsequently sensed cardiac waveform fall within the plurality of target regions.

14. The device of claim 12, wherein the at least one cardiac waveform feature comprises a positive waveform peak or a negative waveform peak.

15. The device of claim 14, wherein the control system is further configured to adjust the one target region based on locations of the positive waveform peak or the negative waveform peak.

16. The device of claim 15, wherein adjustment of the at least one target region is limited by one or both of a predetermined range of the time dimension and a predetermined range of the amplitude dimension.

17. The device of claim 12, wherein adjustment of the at least one target region is limited by one or both of a predetermined amplitude boundary and a predetermined time boundary.

18. The device of claim 17, wherein the predetermined amplitude boundary is an upper boundary.

19. The device of claim 17, wherein the predetermined time boundary is a lower boundary.

20. An implantable medical device, comprising:

means for associating and providing one or more target region attributes with each of a plurality of target regions, the one or more target region attributes including at least sampling rate and each target region having a location, a time dimension, and an amplitude dimension;

means for detecting a cardiac waveform feature;

means for adjusting at least one target region of the plurality of target regions based on a location of the detected cardiac waveform feature and compatibility between attributes of the at least one target region and attributes of the cardiac waveform feature;

means for delivering-a cardiac pacing pulse during a cardiac cycle;

means for detecting features of a subsequent cardiac waveform after delivery of the pacing pulse;

means for determining a cardiac pacing response to the pacing pulse based on whether features of the subsequent cardiac waveform fall within the plurality of target regions; and means for adjusting a pacing energy of the cardiac device based on the cardiac pacing response.

* * * * *